US006927210B1

(12) United States Patent
Thompson et al.

(10) Patent No.: US 6,927,210 B1
(45) Date of Patent: Aug. 9, 2005

(54) ECTOPARASITICIDAL AQUEOUS SUSPENSION FORMULATIONS OF SPINOSYNS

(75) Inventors: William Webster Thompson, Indianapolis, IN (US); Joseph Raymond Winkle, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 313 days.

(21) Appl. No.: 10/048,239

(22) PCT Filed: Aug. 2, 2000

(86) PCT No.: PCT/US00/19558

§ 371 (c)(1), (2), (4) Date: Apr. 30, 2002

(87) PCT Pub. No.: WO01/11964

PCT Pub. Date: Feb. 22, 2001

Related U.S. Application Data

(60) Provisional application No. 60/148,527, filed on Aug. 12, 1999.

(51) Int. Cl.$^7$ .................... A61K 31/7042; C07H 15/24

(52) U.S. Cl. .......................... 514/28; 424/405; 536/6.5; 536/7.1

(58) Field of Search .................. 536/6.5, 7.1; 424/405; 514/28

(56) References Cited

U.S. PATENT DOCUMENTS

| | | | | |
|---|---|---|---|---|
| 5,145,684 A | | 9/1992 | Liversidge et al. | 429/489 |
| 5,202,242 A | | 4/1993 | Mynderse et al. | 435/76 |
| 5,227,295 A | | 7/1993 | Baker | 435/76 |
| 5,362,634 A | | 11/1994 | Boeck et al. | 435/76 |
| 5,496,931 A | | 3/1996 | Boeck et al. | 536/7.1 |
| 5,539,089 A | | 7/1996 | Broughton et al. | 536/6.5 |
| 5,571,901 A | | 11/1996 | Boeck et al. | 536/7.1 |
| 5,591,606 A | | 1/1997 | Turner et al. | 435/76 |
| 5,631,155 A | | 5/1997 | Turner et al. | 435/252.1 |
| 5,670,364 A | | 9/1997 | Mynderse et al. | 435/252.1 |
| 5,670,486 A | | 9/1997 | Mynderse et al. | 514/28 |
| 5,767,253 A | | 6/1998 | Turner et al. | 536/6.5 |
| 5,840,861 A | | 11/1998 | Mynderse et al. | 536/16.8 |
| 5,886,188 A | * | 3/1999 | Bryman et al. | 548/200 |
| 6,001,981 A | | 12/1999 | DeAmicis et al. | 536/7.1 |
| 6,063,771 A | | 5/2000 | Snyder | 514/31 |
| 6,342,482 B1 | | 1/2002 | Snyder | 514/31 |

FOREIGN PATENT DOCUMENTS

| | | |
|---|---|---|
| DE | 2 088 212 | 6/1982 |
| EP | 375 316 | 6/1990 |
| WO | WO 82 02647 | 8/1982 |
| WO | WO 97/00265 | 1/1997 |
| WO | WO 97/33471 | 9/1997 |
| WO | WO 00/60940 | 10/2000 |
| WO | WO 01/11961 | 2/2001 |
| WO | WO 01/11962 | 2/2001 |
| WO | WO 01/11965 | 2/2001 |
| WO | WO 01/12156 | 2/2001 |
| WO | WO 01/19840 | 3/2001 |
| WO | WO 01/40446 | 6/2001 |

OTHER PUBLICATIONS

DeAmicis, et al., "Physical and Biological Properties of the Spinosyn: Novel Macrolide Pest–Control Agents from Fermentation," Americal Chemical Society, Chapter 11, 144–154 (1997).

Spinosad Technical Guide.

Boech, et al., Chemical Abstracts, 114, 9, Abstract No. 80066m (1991).

Kirst, et al., "Discovery Isolation, and Structure Elucidation of a Family of Structurally Unique, Fermentation–Derived Tetracyclic Macrolides," ACS Symposium Series, Synthesis and Chemistry of Agrochemicals III, 504, pp. 214–225 (1992).

Crouse, et al., "Naturally Derived Materials as Products and Leads for Insect Control: The Spinosyns," Rev. Toxicol, 2 pp. 133–146 (1998).

Mertz, F. P., et al., "*Saccharopolyspora spinosad* sp. Nov. Isolated from Soil Collected in a Sugar Mill Rum Still," Int. J. System Bacteriol, 40, pp. 34–39 (1990).

Salgado, V. L., "Studies on the Mode of Action of Spinosad: Insect Symptoms and Physiological Correlates," Pestic. Biochem. Physiol., 60, pp. 91–102 (1998).

Thompson, G. D., et al., "Spinosad A Case Study: An Example from a Natural Products Discovery Programme," Pest. Manag. Sci., 56, pp. 696–702 (2000).

Thompson, G. D., "The Discovery of *Saccharopolyspora spinosad* and a New Class of Insect Control Products," Down to Earth, 52, pp. 1–5 (1997).

Breuninger, J. M., "Conserve SC: A New Product for the Turfgrass and Ornamental Industry," Down to Earth, 53, pp. 1–5 (1998).

Nolting, S. P., "Insect Control in Cotton with Tracer," Down to Earth, 52, pp. 21–27 (1997).

(Continued)

*Primary Examiner*—James O. Wilson
*Assistant Examiner*—Leigh C. Maier
(74) *Attorney, Agent, or Firm*—John C. Demeter

(57) ABSTRACT

The invention provides a stable ectoparasiticidal aqueous suspension formulation of a spinosyn, comprising the spinosyn, or a physiologically acceptable derivative or salt thereof, milled to an average particle size of 1 to 15 microns, a surfactant in an amount effective to facilitate wetting the milled particles; a dispersant in an amount that forms a spinosyn;dispersant weight ration of from 3:1 to 1:5; and water. It also provides a method of controlling an ectoparasite infestation on a small ruminant or companion animal comprising administering an effective amount of such an aqueous suspension formulation.

9 Claims, No Drawings

OTHER PUBLICATIONS

Sparks, et al., "Biological Activity of Spinosyns, New Fermentation Derived Insect Control Agents, on Tobaco Budworm (*Lepidopters: noctuidae*) Larvae," J. Econ. Entomol., 91, pp. 1277–1283 (1996).

Kirst, et al., Tetrahydron Letters, 32(37), 4839–4842 (1991).

Snyder, et al., J. Am. Chem. Soc., 106, 787–789 (1984).

T. C. Sparks, et al., "Biological Characteristics of the Spinosyns: A New Naturally Derived Insect Control Agents," Cotton Insect Research and Control Conference, 1995 Beltwide Cotton Conferences, pp. 903–907.

G. D. Thompson, "Spinosyns: An Overview of New Natural Insect Management Systems," Cotton Insect Research and Control Conference, 1995 Beltwide Cotton Conferences, pp. 1039–1043.

Winkle, et al., "Rheological Studies on Suspension Concentrates," Jun. 12, 1988; XP002153298; Online—http://www.chemsoc.org/chempest/html/2A–0024.html; abstract.

*Agricultural Chemical News,* 195(2), "NAF–85 (spinosad): DowElanco insecticide" (1995).

*Agricultural Chemical News,* 186(2), "Spinosad, NAF–144; DowElanco seeks EPA approval for insecticide" (1995).

Spencer, et al., "Spinosad insect control agent; lack of effects in a one year neurotoxicity screening study in rats," *Fundam. Appl. Tocicol.*; Pt. 2, 211, 30(1) (1996).

Kirst, et al., "Chemistry of Biology of the spinosyns a new class of naturally derived insect control agents," *Abstracts of Papers Americal Chemical Society; 210$^{th}$ American Chemical Society,* 210, Part 1, Abstract No. AGRO061, 1995.

Adan, et al., "Laboratory evaluation of the novel naturally derived compound spinosad against *Ceratitis capitata*," *Pesticide Science,* 48(3), pp. 261–268 (1996).

Boyd, Impact of insecticides on predators of the soybean looper, *Pseudoplusia inc, PhD Dissertation,* The Louisiana State University and Agricultural and Mechanical Col., UMI (9637762), 1996.

King, et al., "Spinosad bait for the Caribbean fruit fly (*Kiptera: tephritidea*)," *Florida Entomologist,* 79(4) pp. 526–531 (1996); ISSN: 0015–4040.

Magnussen, et al., "Characterization of spinosad related residues in poultry tissues and eggs following oral administration," 211$^{th}$ *American Chemical Society National Meeting,* New Orleans, Louisiana, USA, 211:1–2; Agro 43; ISSN 0065–7 (1996).

Saunders, et al., "Degradation of spinosad in aqueous solution," 211$^{th}$ *Americal Chemical Society National Meeting,* New Orleans, Louisiana, USA, 211, Part 1, Abstract No. AGRO048, 1996.

Sparks, et al., "Chemistry and biology of the spinosyns: components of spinosad (Tracer), the first entry into DowElanco's naturalyte class of insect control products," *Proc.—Beltwide Cotton Conf.,* 2:692–696 (1996); ISSN: 1059–2644.

Burton, et al., "Tracer naturalyte insect control physical property attributes," *Proc.—Beltwide Cotton Conf.,* 2:696–697 (1996); ISSN: 1059–2644.

Thompson, et al., "Spinosad and the new naturalyte insect control class," *Proc.—Beltwide Cotton Conf.,* 2:870–872 (1996); ISSN:1059–2644.

Murray, et al., "The effects of spinosad (Tracer) on pests and beneficials," *Australian Cottongrower,* 18:62–64 (1997).

Heller, et al., "Evaluation of experimental DowElanco NAF85 and NAF127 formulations, and Dursban Pro for management of black cutworm on creeping bentgrass, 1996," Anthropod Management Tests, 22:345 (1997).

Heller, et al., "Evaluation of NAF formulations, Dursban Pro, and Scimitar CS for management of black cutworm on creeping bentgrass, 1995," Arthropod Management Tests, 22:346 (1997).

Salgado, et al., "Studies on the mode of action of spinosad, the active ingredient in Tracer insect control," Proc.—Beltwide Cotton Conference, 2:1082–1084 (1997); ISSN: 1059–2644.

Murrey, et al., "The effect of spinosad (Tracer) on arthropod pest and beneficial populations in Australian cotton," *Proc.—Beltwide Cotton Conf.,* 2:1087–1091 (1997); ISSN: 1059–2644.

Sparks, et al., "Penetration of metabolism of spinosyn A in lepidopterous larvae," *Proc.—Beltwide Cotton Conference,* 2:1259–1264 (1997); ISSN: 1059–2644.

*Agricultural Chemical News,* "Success (spinosad): a new DowElanco insecticide formulation," 209: pp. 2–15 (1997).

*Agricultural Chemical News,* "Tracer (spinosad): DowElanco gains insecticide registration," 211; pp. 3–15 (1997).

*Agricultural Chemical News,* "Success (spinosad): DowElanco gains 24(c) insecticide label to use in California," 213; pp. 2–15 (1997).

*Agricultural Chemical News,* "Conserve SC (spinosad): DowElanco gains EPA, USA, insecticide registration," 215; pp. 1–15 (1997).

Yeh, et al., "Application of empore disc extraction for trace analysis of spinosad and metabolites in leafy vegetables, pepper, and tomatoes by high–performance liquid chromatography with ultraviolet detection," *Journal of Agricultural and Food Chemistry,* vol. 45, No. 5, pp. 1746–1751; ISSN 0021–8561, 1997.

Boyd, et al., "Residual toxicity of selected insecticides to heteropteran predaceous species (*Heteroptera: lygaeidae, nibidae, pentatomidae*) on soybean," *Environ. Entomol.,* vol. 27, No. 1, pp. 154–160 (1998).

Kolarid, et al., "Colorado potato beetle control, 1997," *Arthropod Management Tests,* vol. 23; pp. 124–126 (1998).

Cowles, "Effect of spinosad formulations and other miticides on twospotted spider mite, 1995," *Arthropod Management Tests,* vol. 23, pp. 342–343 (1998).

Kjaer, et al., "The impact of phenology, exposure and instar susceptibility on indecticide effects on a chrysomelid beetle population," *Prestic. Sci.,* vol. 52, No. 4, pp. 361–371 (1998).

Marty, et al., "The maternal and developmental toxicity of spinosad in Sprague–dawley rats and New Zealand White rabbits," *Teratology,* vol. 57, pp. 4–5 (1998).

Salgado, et al., "Studies on the mode of action of spinosad: The internal effective concentration dependence of neural excitation," *Pesticide Biochemistry and Physiology,* vol. 60, No. 2, pp. 103–110 (1998).

Boyd, et al., "Susceptibility of predaceous hemipteran species to selected insecticides on soybean in Louisiana," *Journal of Economic Entomology,* vol. 91, No. 2, pp. 401–409 (1998).

Woodburn, et al., "Bioconcentration and metabolism of a unique insecticide (spinosyn) by the Rainbow trout," *Second World Congress of the Society of environmental toxicology and chemi,* PT127; pp. 5–9 (1995).

Stoltz, et al., "Colorado potato beetle control with foliar sprays, 1995," *Arthropod Management Tests,* vol. 21, pp. 168–169.

Sewell, et al., "Irish potato, control of Colorado potato beetle, 1995," *Arthropod Management Tests,* vol. 21, pp. 158–159.

Olson, et al., "Potato Colorado potato beetle control with spinosad, 1995," *Arthropod Management Tests,* vol. 21; pp. 154–155.

Noetzel, et al., "Control of resistant Colorado potato beetle, Blaine, MN, 1995," *Arthropod Management Tests,* vol. 21, pp. 149.

Noetzel, et al., "Colorado potato beetle control, Crookston, MN, 1995," *Arthropod Management Tests,* vol. 21, pp. 145–146.

Hedin, et al., "Physical and biological properties of the spinosyns: novel macrolide pest–control agents from fermentation," Phytochemicals for Pest Control, Chapter 11, 1995 *International Chemical Congress of Pacific Basin Societies;* ACS Symposium Series 658, pp. 144–153.

Sears, et al., "Effects of various rates and combinations of insecticides on the control of Colorado potato beetle (CPB) (1995)," *Pest Management Research Report—Insects and Diseases,* ICAR: 86100104; pp. 159–161; Report No. 061 (1995).

J. M. Edwards, et al., "Potential of Spinosad as a Control Agent for Diptera," ESA Annual Meeting, Las Vegas, Nevada, Dec. 17–21 (1995).

* cited by examiner

ECTOPARASITICIDAL AQUEOUS SUSPENSION FORMULATIONS OF SPINOSYNS

This application is the National Stage of International Application No. PCT/US00/19558, filed Aug. 2, 2000, which claims the benefit of U.S. Provisional Application Ser. No. 60/148,527, filed Aug. 12, 1999.

There are many types of ectoparasiticidal formulations. These types include emulsifiable concentrates, wettable powders, organic solvent solutions and suspensions. Many of these formulations require the use of an organic solvent. For example, an organic solvent must be used when preparing an oil-in-water emulsifiable concentrate. Organic solvents, however, are typically regarded as having adverse environmental or ecological effects, and they can add to the overall toxicity of the formulation. Wettable powders can be dispersed in tank mix formulations without organic solvents, but they are generally inferior to other formulations in biological effect and handling characteristics. There is a need, therefore, for safer formulations such as aqueous formulations.

Spinosyns (also known as A83453 factors) are known agricultural insecticides. Because of their low toxicity to animals and humans, spinosyns are considered to be environment-friendly, "green" pesticides. It is desirable to formulate spinosyns to maintain this "green" profile.

The spinosyns were also known to have some ectoparasiticidal activity, i.e., they had in vitro activity against mosquito larvae, black blowfly larvae and adult stable flies, which are members of the insect order Diptera, and transient systemic activity against larval blowfly and adult stable fly in guinea pigs and sheep. For these studies, the spinosyns were administered in aqueous polyvinylpyrrolidone or in polyethylene glycol (see, U.S. Pat. No. 5,571,901, col. 26–32).

The spinosyns have recently been found to be useful in controlling ectoparasites on sheep and companion animals. Thus, useful formulations of spinosyns with low toxicity and increased stability are potentially valuable in combating ectoparasites, thereby preventing the diseases such pests often carry.

Aqueous formulations of spinosyns would be most desirable. Unfortunately, spinosyns have low solubility in water and are unstable in aqueous solution.

This invention provides a stable aqueous suspension formulation suitable for spinosyns. These aqueous suspension formulations offer several advantages over previous non-aqueous or solvent-containing spinosyn formulations. Their advantages include greater chemical, biological and thermal stability and improved ease of use.

The ratio of active ingredient to dispersant is a unique characteristic of the formulations of this invention. Generally, aqueous suspension formulations have a ratio of active ingredient to dispersant ratio in the range of about 5:1 to about 25:1. The formulations of this invention, however, have higher amounts of dispersant, bringing the spinosyn to dispersant ratio to from about 3:1 to about 1:5. Previous formulations of spinosyns with relatively low concentrations of dispersant, as compared to the higher concentrations in the present formulations, tended to lack homogeneity and predictability with respect to expected concentrations upon dilution. This result was surprising because it was thought that spinosyns at such low concentrations would be completely solubilized.

Increasing the concentration of dispersant in the aqueous suspensions produced another unexpected result. When the formulations with increased dispersant concentration were diluted to form aqueous dip solutions containing 5 ppm to 25 ppm of spinosyn, the diluted solutions had homogenous spinosyn concentrations throughout the dip solution, a very beneficial effect.

In particular, this invention provides a stable ectoparasiticidal aqueous suspension formulation comprising an ectoparasiticidal amount of a spinosyn, or a physiologically acceptable derivative or salt thereof, milled to an average particle size of about 1 to about 15 microns, and a surfactant in an amount effective to facilitate wetting the milled particles; a disperant in an amount sufficient to form a spinosyn:dispersant weight ratio of from 3:1 to about 1:5; and water.

Particularly useful stable ectoparasiticidal aqueous suspension formulations of this invention are those;

a) wherein the amount of spinosyn is from about 0.1 to about 50 weight percent of the formulation;

b) wherein the dispersant is ionic;

c) wherein the amount of surfactant is about 0.1 to about 10 weight percent of the formulation;

d) which further comprise about 0.3 to about 5 weight percent of a mineral thickener, e) which further comprise about 0.05 to about 3 weight percent of a gum, and f) which further comprise an antimicrobial agent acceptable for topical veterinary applications in an amount effective to prevent microbial growth in the suspension.

Other preferred spinosyn-containing formulations comprise about 25 gram/liter of spinosad, a condensed napthalene sulfonic acid as a dispersant, propylene glycol as an antifreeze agent and humectant, a surfactant, a mineral suspending aid, a xanthan gum suspending aid, an antimicrobial agent, a foam control agent, and deionized water (vehicle).

The components can be mixed in various proportions to achieve the characteristics desired in the formulation.

The formulations of this invention are aqueous suspensions. By "aqueous" is meant that the formulation is a water-based system, i.e., no organic solvents are included in the formulation.

The fact that the present compositions are water-based is important from a chemical stability perspective. Aqueous suspension formulations of this invention containing 25 g/L of spinosad have been shown to be chemically stable at ambient and elevated temperatures for at least six months as indicated by HPLC analysis. The formulations are physically stable and readily dispersible in water for use. For topical dips, sprays, and other applications, having the spinosyn delivered in water is a great advantage. The formulations can be used without dilution (neat), either as a pour-on or spot-on, or they can be diluted to form an homogeneous aqueous solution suitable for use as a topical dip.

An unexpected advantage is that these formulations provide whole animal ectoparasiticidal effectiveness when applied as a pour-on or spot-on application. When the formulations are used as topical dips, for example, they allow easy whole treatment of larger animals such as sheep, goats, and camellids, etc., with minimal "stripping" of the formulation from the diluted dip as the number of animals treated in a dip pool increases.

The insecticidal component in these formulations is a spinosyn, or a derivative or salt thereof. Spinosyns are naturally-derived macrolides produced by fermentation of *Saccharopolyspora spinosa*. The fermentation produces multiple factors, including spinosyn A and spinosyn D (also called A83543A and A8354D). Spinosyn A and spinosyn D are the two spinosyns that are most active as insecticides. An agricultural product comprised mainly of these two spinosyns is available commercially under the generic name "spinosad" for field applications.

Spinosyn A was the first spinosyn isolated and identified from the fermentation broth of *Saccharopolyspora spinosa*. Subsequent examination of the fermentation broth revealed that *S. spinosa* produced a number of spinosyns that have been called spinosyns A to J (A83543A to J). Additional spinosyns, denominated K to W, have been identified from mutant strains of *S. spinosa*. The various spinosyns are characterized by differences in the substitution patterns on the amino group of the forosamine, at selected sites on the tetracyclic ring system and on the 2N,3N,4N-(tri-O-methyl) rhamnose group.

The term "spinosyn" as used herein refers to one or more spinosyn factor (spinosyn A, B, C, D, E, F, G, H, J, K, L, M, N, O, P, Q, R, S, T, U, V, W or Y), an N-methyl derivative of one or more spinosyn factor, or a combination thereof. For convenience, the term "spinosyn" or "spinosyn component" will also be used herein to mean a spinosyn factor, a physiologically acceptable derivative or salt of a spinosyn factor, or a combination thereof.

Boeck et al. described spinosyns A–H and J (which they called A83543 factors A, B, C, D, E, F, G, H and J), and salts thereof in U.S. Pat. No. 5,362,634 (issued Nov. 8, 1994); U.S. Pat. No. 5,496,932 (issued Mar. 5, 1996); and U.S. Pat. No. 5,571,901 (issued Nov. 5, 1996). Mynderse et al. described spinosyns L–N (which they called A83543 factors L, M and N), their N-dimethyl derivatives, and salts thereof, in U.S. Pat. No. 5,202,242 (issued Apr. 13, 1993); and Turner et al. described spinosyns Q–T (which they called A83543 factors Q, R, S and T), their N-dimethyl derivatives, and salts thereof, in U.S. Pat. No. 5,591,606 (issued Jan. 7, 1997) and U.S. Pat. No. 5,631,155 (issued May 29, 1997). Spinosyns K, O, P, U, V, W and Y are described, for example, by Carl V. DeAmicis, James E. Dripps, Chris J. Hatton and Laura I. Karr in American Chemical Society's Symposium Series: Phytochemicals for Pest Control, Chapter 11, "Physical and Biological Properties of Spinosyns: Novel Macrolide Pest-Control Agents from Fermentation", pages 146–154 (1997).

The spinosyns can be isolated in the form of salts that are also useful in the compositions and methods of this invention. The salts are prepared using standard procedures for salt preparation. For example, spinosyn A can be neutralized with an appropriate acid to form an acid addition salt. Representative suitable acid addition salts include salts formed by reaction with either an organic or inorganic acid, for example, sulfuric, hydrochloric, phosphoric, acetic, succinic, citric, lactic, maleic, fumaric, cholic, pamoic, mucic, glutamic, camphoric, glutaric, glycolic, phthalic, tartaric, formic, lauric, stearic, salicylic, methanesulfonic, benzenesulfonic, sorbic, picric, benzoic, cinnamic and like acids.

When preparing the formulations of this invention, the spinosyn component should be milled to an average particle size of from about 1 to about 15 microns in order to form the most suitable suspension. A preferred average particle size is from about 2 to about 7 microns, especially 3 to 7 microns. The milling is accomplished by a "wet milling" process in which the spinosyn is exposed to sufficient surfactant to facilitate wetting the milled particles.

The formulations of this invention comprise an ectoparasiticidal amount of the spinosyn component. By "ectoparasiticidal amount" is meant an amount that effectively controls or kills a target insect, parasite, or ectoparasite when applied to an animal that either has an insect, parasite or ectoparasite infestation or is susceptible to acquiring such an infestation. As those in the art understand, the amount of spinosyn that is ectoparasiticidal will vary, depending upon a number of factors, including the insect or parasite being controlled, the host animal being treated, other components of the formulation and the route of administration.

In order to provide an ectoparasiticidal amount and form a suitable suspension, the spinosyn concentration should be in the range of from about 0.02 to about 50 percent by weight of the formulation. Preferably, the spinosyn concentration should be in a range of from about 0.1 to about 50 weight percent of the formulation Even more preferably, the spinosyn component is present in an amount of from about 2 to about 5 weight percent of the formulation. For example, a useful formulation is one wherein 25 g of the spinosyn component is present per liter of the formulation.

The formulations of this invention also include a dispersant. A dispersant is a compound that is able to counteract particle-to-particle attraction within an aqueous suspension without significant reduction in surface tension of the aqueous suspension vehicle (i.e., the addition of the dispersant does not reduce the surface tension of water below 40 dynes/cm). A dispersant has physicochemical properties that allow the dispersant to orient itself between particles of active ingredient and, by virtue of the dispersant's size and/or charge, reduce the cohesiveness or attraction of the active ingredient particles for each other. In addition to imparting physical stability to the aqueous mixture, dispersants may also aid in the redispersibility of a diluted spray mixture. The dispersing agent should be carefully selected and used to avoid problems such as agglomeration, sedimentation and flocculation. Any dispersant that interferes with particle-to-particle attraction or cohesiveness by virtue of size and/or charge is useful as a dispersant for purposes of the present invention.

Both ionic and nonionic dispersants are useful in the formulations of this invention, but ionic dispersants are preferred. Examples include lignosulfonic acids and salts thereof, polymerized alkyl, arylalkyl or naphthalene sulfonic salts, comb polymeric dispersants (such as ATLOX 4913™, Uniqema), condensed formaldehyde/naphthalene sulfonic acid and salts thereof, sodium dioctyl sulfosuccinate and high molecular weight anionic dispersants. An especially useful dispersant is a condensed formaldehyde/napthalene sulfonic acid or a salt thereof. A suitable condensed napthalene sulfonic acid dispersant is available from Kenkel Corp. as LOMAR PWA.

The type of water used in these aqueous formulations is not critical. For example, it can be tap water or deionized water. The water can have a pH range of from about 5 to about 10, with an ideal range pH of 6 to 9.

The surfactant used in the formulations of this invention should maintain the resulting suspension of milled particles at a low viscosity and allow a high percentage recovery of milled solids after processing. A surfactant is a compound that is surface active and reduces the surface tension of water to $\leq 40$ dynes/cm. Although anionic, cationic, nonionic and amphoteric surfactants can be used in these formulations, nonionic surfactants are preferred. Examples of surfactants that are particularly useful include straight and branched chain octyl and nonyl phenols, straight and branched chain alcohol ethoxylates, and alkyl aryl ether ethoxylates.

The surfactant should be present in an amount sufficient to facilitate wetting the milled particles of the spinosyn component. Generally, the amount of surfactant is from about 0.1 to about 10 weight percent of the formulation. A preferred amount of surfactant is from about 0.1 to about 5 weight percent of the formulation.

Often nonionic surfactants will efficiently wet solids without tending to solubilize micron-sized particles after milling. Certain block copolymers of polyoxypropylene-polyoxyethylene that contain ethylene oxide are particularly useful surfactants in the formulations. These surfactants vary in wetting ability as the ethylene oxide content varies. Examples are the PLURONIC series (BASF). PLURONIC P-103™, PLURONIC P-104™, and PLURONIC P-123™ surfactants are especially preferred. Qualitative wetting tests of these surfactants in water indicated an ability to wet technical grade spinosad in less than 30 seconds.

A number of other optional components may be added to the formulations of this invention. Examples of these include:
suspending aids or thickeners, UV absorbing compounds, antimicrobial agents, viscosity modifying compounds, antifoam agents or defoamers, dyes,
substantive agents, perfumes,
antifreeze agent, deodorants,
humectants, and
physiologically or dermatologically acceptable carriers, diluents, excipients or adjuvants.

Suspending aids or thickeners aid in structure formation and rheology building of the aqueous suspension formulations. These agents impart physical stability to the suspensions. Thickeners increase the viscosity of the formulation, thereby aiding in the suspension of active ingredient. Many types of thickeners are available. These include gums and natural polysaccharides, mineral thickeners, and synthetic polymeric thickeners.

The gums and natural polysaccharides class of thickeners includes numerous gums, starches, celluloses, and other polysaccharides. Examples of gums and natural polysaccharides are xanthan gum, guar gum, locust bean gum, carrageenan, pectin, tragacanth and tamarind gum.

Examples of mineral thickeners are inorganic clays, fumed and precipitated silica, mixed metal hydroxides and mixed metal silicates. Among the inorganic thickeners are various commercially available silica thickeners, including hydrophilic silicas and hydrophobic silicas. Hydrophobic amorphous fumed silicas are also useful as the thickening additive. Examples of hydrophobic silicas are AEROSIL R-972 and AEROSIL R-974 from Degussa Corporation, Akron, Ohio.

A preferred mineral thickener for use in the formulations is a complex colloidal magnesium aluminum silicate refined and derived from natural smectite clays. R. T. Vanderbilt Co. makes a suitable mineral suspending aid called VEEGUM and a xanthan gum suspending aid called RHODOPOL 23.

Synthetic polymeric thickeners are anionic, nonionic, cationic or hydrophobically modified polymers. Examples include compounds such as sodium polyacrylates, alkyl and alkyloxycelluloses (including sodium carboxymethyl cellulose, methyl cellulose, ethoxylated cellulose, hydroxypropylmethyl cellulose, hydroxyethyl cellulose and modified hydroxyethyl cellulose), microcrystalline cellulose, starches and modified starches, polyvinylpyrrolidone, polyethylene glycol of molecular weight from 2000 to 4,000,000, and mixtures thereof. Preferably, the polymer is selected from the group consisting of sodium polyacrylate, hydroxyethyl cellulose, cetyl hydroxyethyl cellulose, polyvinylpyrrolidone and polyquaternium-10.

Other compounds are also useful as thickening agents or suspending aids in the formulations. For example, sugars, salts and other small molecules such as urea can be used to increase the density of the water used in the aqueous formulation, thus aiding in the suspension of the active ingredient particles. These compounds are added to the formulation in an amount sufficient to increase the density of the aqueous solution to counteract the physical forces that favor settling out of the suspension particles.

The amount of thickener or suspending aid and the ratio of the suspending aid to the spinosyn component vary depending on the desired concentration of the spinosyn component in the formulation. In general, the amount of thickener is from about 0.05 to about 8 weight percent of the formulation. For example, a useful formulation containing 200 g/L of spinosad and 0.2% (w/w) xanthan gum contained 1% (w/w) of complex colloidal magnesium aluminum silicate (1:5 ratio), whereas formulations with lower amounts of active or solids content, such as 50 g/L or 25 g/L of spinosad, and 0.2% (w/w) xanthan gum contained 2% (w/w) of complex colloidal magnesium aluminum silicate (1;10 ratio) in the final formulation.

As a general rule, suspensions with a higher content of solids or active ingredient are more efficient to wet mill and suspend in water than suspensions with lower content of solids or active ingredient. Suspensions with a lower concentration of active ingredient have a high water content, requiring the addition of proportionately higher amounts of suspending aids to suspend the solids. The viscosity of the final aqueous suspension formulation should be at a minimum so it can be easily poured from the container and mixed with water for use.

Antimicrobial agents are often added to formulations to prevent unwanted microbial growth, particularly if a component of the formulation supports such growth. For example, when xanthan gum is used as a thickening agent to suspend solids and build viscosity, the addition of an antimicrobial agent prevents microbial attack of the gum and loss of product viscosity.

A variety of antimicrobial agents are useful for this purpose. Certain chemicals such as 1-(3-chloroallyl)-3,5,7-triaza-1-azoniaadamantane chloride and 1,2-benzisothiazolin-3-one are examples of particularly useful antimicrobial agents. The former compound is available from Dow Chemical Company as DOWICIL 75™ preservative; and an aqueous solution of the latter in di(propylene glycol) is available from Zeneca Biocides as PROXEL GXL™. The latter antimicrobial agent is stable in the presence of amines and amine-containing compounds such as spinosad and possesses a broad spectrum of activity against microorganisms.

When the antimicrobial component is a liquid and the thickening agent is suspended in an agent such as propylene glycol before hydration, it is convenient to incorporate the antimicrobial agent in the suspending agent.

Typically, the aqueous flowable formulations of this invention may contain from about 0.01 to about 0.5 weight percent of an antimicrobial agent, with a preferred range of 0.04 to about 0.3 weight percent. For example, a formulation of this invention contained xanthan gum as a thickener and an aqueous solution of 1,2-benzisothiazolin-3-one in di(propylene glycol) at a level of 0.2% w/w (2000 ppm). This level of antimicrobial agent was effective to preserve the gum.

An antifoam agent or defoamer is a useful optional component in the present formulations. Poly (dimethylsiloxane) antifoams are particularly useful. They can be initially incorporated into the grind batch of spinosad for foam control. Examples of these agents are ANTIFOAM A™ and ANTIFOAM C™, available from Dow Corning. The former is a 100% active antifoam. The latter, which is a 30% emulsion of poly(dimethylsiloxane) in water, was found to be more effective in processing. It is advantageously incorporated into the formulation at about 0.2% w/w. Other examples of commercially available antifoam agents useful in the present formulations include ANTIFOAM FG-10, ANTIFOAM DB-100, and ANTIFOAM AF-100 (all available from Dow Corning). Other antifoam agents are also useful in these formulations.

A substantive agent is another ingredient that may be added to the present formulations. The term "substantive agent" means a compound that increases the binding or retention of an active ingredient (in this case the spinosyn component) to the surface layer of the stratum corneum or to hair. Preferred substantive agents also aid in resisting removal of the active component by water or by physical contact, such as rubbing. Examples of useful substantive agents include acrylates, polyvinyl acetates, and polyvinyl alcohols.

This invention also relates to a method of manufacturing a stable ectoparasiticidal aqueous suspension formulation, said method comprising:

(1) wet-milling a composition containing a spinosyn, or a physiologically acceptable derivative or salt thereof, with a surfactant, a dispersant, an antifoam agent and water to form a "grind composition" in which the spinosyn has an average particle size is from about 1 to about 15 microns;

(2) blending an aqueous suspension containing about 2 to about 10 percent by weight of a mineral thickener with a dispersion composition containing about 1 to about 4 percent by weight of a gum in a $C_2$–$C_4$ alkylene diol to form a "hydrated suspension composition" containing about 0.5 to about 8 percent by weight of the mineral thickener; and (3) diluting a first volume of the grind composition with a second volume of the hydrated suspension composition sufficient to provide the desired spinosyn concentration.

Alternatively, the formulations of this invention can be prepared by (1) making a concentrated aqueous suspension of the spinosyn component, (2) diluting the concentrate to appropriate spinosyn concentrations for use as a pour-on, spot-on or dip concentrate, and then (3) adding a sufficient amount of dispersant to bring the ratio of spinosyn to dispersant into the range of about 3:1 to about 1:5.

A nonionic surfactant (such as PLURONIC P-123™) is a preferred surfactant to incorporate into the aqueous suspension of spinosyn. A suitable "hydrated suspension batch" is formed by blending a hydrated suspension of a complex colloidal magnesium aluminum silicate suspending aid (such as VEEGUM) with a xanthan gum hydrated in propylene glycol (such as RHODOPOL 23™). The hydrated suspension batch and additional water as needed are blended with the grind batch to prevent syneresis, or separation of clear watery fluid from suspended milled solids. The appropriate amount of the hydrated suspension batch to be blended with the grind batch to complete the formulation is determined based upon the percent recovery of the grind batch after particle size reduction.

The following order of addition of formulation inerts is recommended to prepare the hydrated suspension, which is used to control product viscosity and prevent syneresis of milled spinosad: (1) add all the complex colloidal magnesium aluminum silicate to deionized water with high speed stirring and allow to fully hydrate; (2) add the xanthan gum to the propylene glycol with stirring to fully disperse the gum in the glycol; and (3) instantly hydrate the xanthan gum in water by the addition of item (2) to item (1) with stirring. Do not incorporate excessive amounts of air into the suspension.

In another aspect, this invention provides an article of manufacture, comprising packaging material and a formulation for controlling an ectoparasite infestation on a small ruminant or companion animal contained within said packaging material, wherein said formulation comprises:

a) a unit dose of an ectoparasiticidal amount of a spinosyn, or a physiologically acceptable derivative or salt thereof, milled to an average particle size of from about 1 to about 15 microns, and a surfactant in an amount effective to facilitate wetting the milled particles;

b) a dispersant in an amount sufficient to form a spinosyn:dispersant weight ratio of about 3:1 to about 1:5; and c) water; and wherein said packaging material comprises a label or package insert with instructions for administering the dose to the animal.

This invention also encompasses a method of controlling an ectoparasite infestation on a small ruminant or companion animal, comprising administering to the animal a formulation comprising an ectoparasiticidal amount of a spinosyn, or a physiologically acceptable derivative or salt thereof, milled to an average particle size of from about 1 to about 15 microns, and a surfactant in an amount effective to facilitate wetting the milled particles; a dispersant in an amount sufficient to form a spinosyn:dispersant weight ratio of from 3:1 to 1:5; and water.

The term "controlling" refers to either eliminating or ameliorating a current infestation or preventing an infestation on a susceptible animal. By "animal" is meant a small ruminant or a companion animal. Small ruminants include sheep, goats and camellids. Examples of companion animals are dogs, cats, horses and other pets owned and maintained in close association with humans as part of the human-animal bond.

A preferred formulation for use in this method is an aqueous suspension comprising from about 1 to about 50 weight percent of a spinosyn, a dispersant in an amount sufficient to bring the spinosyn:dispersant ratio to about 3:1 to about 1:5, and about 0.1 to about 5 weight percent of a surfactant.

In this method, the aqueous suspension is preferably applied topically in a pour-on or spot-on treatment protocol. In a pour-on or spot-on treatment, the formulation is applied directly to the animal's hair and/or skin on the head, neck, shoulders or back, with the treated area being less than 10 percent of the surface area of the hair and skin of the animal.

Optional ingredients that can be included in the aqueous suspension used as a pour-on or spot-on include about 1 to about 5 weight percent of a suspending aid selected from mineral thickeners and gums, about 0.5 to about 2 weight percent of an ionic dispersant, up to 10 percent (w/w) of a polymeric substantive agent to increase substantiveness of the formulation to hair and/or skin, and an antimicrobial agent in an amount effective to prevent the growth of microorganisms in the aqueous suspension.

An advantage of this method, and of the aqueous suspensions of this invention, is that the spinosyn only needs to be applied weekly or bi-weekly. This characteristic allows the animal's caretaker to minimize the effort needed to control the ectoparasites on the animal by lengthening the period between applications. Another advantage is that the formulations can be applied rapidly and easily. Further, the cost of application equipment used with these formulations is very low in comparison with that required for other ectoparasiticide formulations.

In addition to the pour-on and spot-on applications, the aqueous spinosyn suspensions of this invention can also be used in water-dilutable dip and spray applications. Further, the aqueous suspension formulations can also be useful for systemic administration of the active ingredient, such as by use in feed or as an injectable formulation.

The following examples illustrate the formulations of this invention. In the examples, the spinosad used ("spinosad, technical grade") was a product available commercially from Dow Agrosciences. In preparing the formulations the spinosad was milled to a particle size of from 3 to 7 microns.

EXAMPLE 1

Effect of Dispersant on Spinosad Concentration

To examine whether addition of a dispersant allows for greater predictability of diluted concentrations when compared to aqueous suspensions lacking such dispersants, laboratory studies were conducted in which aqueous suspensions were evaluated in the presence and absence of dispersant. Two groups of aqueous suspensions containing 25 g/L of spinosad were prepared, one group containing a dispersant and one without dispersant. The dispersant used was an ammonium salt of sulfonated naphthalene condensate that was about 45% solids. It was used at concentrations of 4 to 5% weight/weight to give about 2% active dispersant on a solids basis.

The suspensions were diluted in a sufficient amount of tap water or deionized water at various pH levels to dilute the spinosad to a theoretical concentration of 100 ppm. Samples were evaluated for actual spinosad concentration immediately upon dilution and after 24 hours.

Table 1 compares the spinosad concentrations in two types of water at three pH levels at the time the samples were initially diluted to a theoretical concentration of 100 ppm and 24 hours after dilution.

TABLE 1

Effect of Dispersant on Spinosad Concentration
SPINOSAD (ppm)

| Water | Initial Concentration | | 24 Hr. Post-dilution Concentration | |
|---|---|---|---|---|
| | No Dispersant | Dispersant | No Dispersant | Dispersant |
| Deionized | | | | |
| (pH = 4.0) | 74.1 | 92.7 | 59.7 | 70.4 |
| (pH = 7.0) | 65.1 | 92.2 | 27.8 | 73.0 |
| (pH = 10.0) | 60.5 | 86.3 | 29.1 | 71.2 |
| Tap | | | | |
| (pH = 4.0) | 68.2 | 90.2 | 32.0 | 66.1 |
| (pH = 7.0) | 72.1 | 85.2 | 23.5 | 65.9 |
| (pH = 10.0) | 76.7 | 94.1 | 37.4 | 64.6 |

As Table 1 shows, including a dispersant greatly improved spinosad concentrations in aqueous formulations at pH levels of 4, 7, and 10 in both soft (deionized) and hard (tap) waters. The dispersant also aided the resuspension properties (remixing properties) of the formulation after quiescent settling of the solids from suspension.

EXAMPLE 2

Effectiveness of Aqueous Suspension Formulation of Spinosad (1 g/L) as an Ectoparasiticide A dip formulation study for the control of *Bovicola ovis* Hartley Strain on sheep was conducted. In this study an aqueous suspension (AS) formulation containing 1 g/L of spinosad was prepared and diluted 1:5000 in water to form a dip solution with a spinosyn concentration of 0.2 ppm. Duration of study was 56 days, with lice counts taken initially, 7, 14, 28, 42, and 56 days after treatment.

Table 2 summarizes the results of this study.

TABLE 2

Lice Control in Sheep with Spinosad AS Dip Formulation

| Group | Lice Counts (geometric mean) | | | | | |
|---|---|---|---|---|---|---|
| Days post-treatment | 0 | 7 | 14 | 28 | 42 | 56 |
| Control | 203.4 | 187.3 | 180.1 | 219.8 | 208.5 | 199.1 |
| Aq Suspension (0.2 ppm) | 188.5 | 6.5 | 5.8 | 11.4 | 18.5 | 18.3 |

As Table 2 shows, the dip containing 0.2 ppm of spinosad gave excellent lice control on sheep initially and after 56 days. A preferred dose of spinosad in dip water for 100% effective lice control is considered to be 1.0 ppm, to allow for a 5-fold confidence factor.

EXAMPLE 3

Spinosad Formulation Stability Studies

Study 1

Several spinosad-containing dip formulations were subjected to prolonged storage at 40° C. in a chemical storage stability study. Dips 1 and 2 were emulsifiable concentrates of spinosad. In Dip 1 the spinosad was formulated in an aromatic hydrocarbon solvent with a specific gravity of 0.9 at 60 F (Aromatic 150), and in Dip 2 it was formulated in methyl oleate as the solvent. Dip 3 was an aqueous suspension of spinosad. The concentration of spinosad present in the formulations was measured after the compositions were exposed to this elevated temperature for 0, 7, 14, 28 and 87 days. Measurements were made by analytical HPLC. Initial (Day 0) measurements were listed as 100% for purposes of comparing the concentrations of active ingredient present at later times. The results of this study are listed in Table 3.

TABLE 3

Spinosad Stability in Three Dip Formulations at 40° C.

Spinosad Concentration, Percent of Initial

| | Dip 1 Concentrations | | Dip 2 Concentrations | | Dip 3 Concentrations | |
|---|---|---|---|---|---|---|
| | 0.2 g/L | 1 g/L | 0.2 g/L | 1 g/L | 0.2 g/L | 1 g/L |
| Initial Day | 100 | 100 | 100 | 100 | 100 | 100 |
| Day 7 | 114.2 | 86.2 | 91.3 | 92.9 | 105.8 | 103.6 |
| Day 14 | 95.2 | 76.7 | 86.9 | 89.7 | 100 | 95.1 |
| Day 28 | 80.9 | 59.4 | 85.6 | 85 | 105.8 | 100 |
| Day 87 | 19 | 43.1 | 82.6 | 110.2 | 111.7 | 97.5 |

As Table 3 shows, the emulsifiable concentrate formulations were not stable, but the aqueous suspension formulation was chemically stable.

Study 2:

Two formulations containing 25 g/L of spinosad were prepared, one an aqueous suspension (AS) and the other an aqueous solution. They were stored at both ambient temperature (i.e., room temperature) and at 50° C. to compare the stability of the two formulations. HPLC quantitation was used to measure spinosad concentration at various points in time. The results of this study are listed in Table 4.

TABLE 4

Stability of Spinosad at 25 g/L in Aqueous
Suspension and Solution Formulations

Spinosad Concentration, Percent of Initial

| | Aqueous Suspension | | Aqueous Solution | |
|---|---|---|---|---|
| Days | Ambient | 50° C. | Ambient | 50° C. |
| 0 | 100 | 100 | 100 | 100 |
| 7 | 107.7 | 100 | 100.3 | 93.4 |
| 14 | 115.4 | 107.7 | 98.6 | 88.9 |
| 21 | 102.3 | 119.2 | 99.3 | 77.9 |
| 28 | 95.7 | 97.7 | 96.9 | 73.4 |
| 42 | 97.7 | 98.5 | 96.7 | 67.1 |
| 70 | 101.5 | 105.4 | 79.9 | 50.8 |
| 98 | 103.8 | 104.2 | 56.9 | — |

At this study shows, the spinosad 25 g/L aqueous suspension was chemically stable at temperatures ranging from ambient to approximately 50° C. for 98 days; however, the spinosad aqueous solutions did not exhibit long-term chemical stability at either ambient or elevated temperatures.

EXAMPLE 4

Spinosad Stripping from Dip Water

Two trials were conducted to determine the degree to which spinosad is removed (stripped) from dip water after dipping sheep. In the trials, spinosad dip tank concentrations of 50 ppm and 5 ppm were prepared from an aqueous suspension containing 25 g/L of spinosad. Both trials involved dipping 10 Dorset-cross shorn sheep in 70 gallons (265 liters) of treated water. Each animal was dipped for 30 seconds duration, with the head immersed twice. Samples of dip water were taken for HPLC analysis, initially and after each sheep was dipped. The pH of the water was also determined after each animal was dipped. A dip tank concentration of 5 ppm of spinosad should provide lice control on sheep. Spinosad is in true solution at 5 and 50 ppm concentration.

During the 50 ppm trial, approximately 1.5 gallons (5.7 liters) of dip water were lost from the dip tank for each animal dipped. The pH of the dip water increased after each sheep was dipped in the tank. The concentration of spinosad in the dip water decreased approximately 4% after dipping ten sheep.

During the 5 ppm trial, approximately 2.1 gallons (8 liters) of dip water were lost from the dip tank for each animal dipped. Again, the pH of the dip water increased after each sheep was dipped in the tank. The concentration of spinosad in the dip water decreased approximately 14% after dipping ten sheep.

Thus, the study showed similar changes in pH and active ingredient concentration associated with dipping sheep in diluted aqueous suspensions with final concentrations of 50 ppm and 5 ppm. These sheep studies indicated minimal stripping of spinosad from the diluted dip water after dipping a limited number of animals.

EXAMPLE 5

Aqueous Suspension Formulation of Spinosad (25 g/L) Prepared by Batch Wet Milling Process A 25 g/L concentrate of spinosad having the following components was prepared as follows:

| Component | Quantity, % w/w |
|---|---|
| Spinosad, technical grade @ 92.0% | 2.7 |
| Dispersant Solution (LOMAR PWA) (44%) | 4.5 |
| Mineral Thickener (VEEGUM) | 1.0 |
| Antimicrobial Agent (PROXEL GXL) | 0.2 |
| Propylene Glycol | 10.0 |
| Xanthan Gum (RHODOPOL 23) | 0.2 |
| Surfactant (PLURONIC P123) | 1.0 |
| Antifoam, 30% solution (ANTIFOAM C) | 0.2 |
| Deionized Water | 80.2 |

Three stock solutions were prepared in separate agitated stainless steel vessels. A 10% stock solution (Solution A) of the surfactant was made. The surfactant used was a paste at 20° C. and so was warmed to 50° C. to liquefy it. Moderate mixing was required for its dissolution/dispersion in water.

A second stock solution (Solution B) of the mineral thickener as a 5–10% hydrate (with 5% being most typical) was prepared in water using a high shear mixer (i.e. Cowles disperser) to assure dissolution/dispersion. The cycle time required was approximately 4 hours.

In the third stock solution (Solution C), the xanthan gum was hydrated by making a slurry of the dried powder in propylene glycol containing the full amount of the antimicrobial agent and dispersing the slurry in water under moderate shear. Typically, xanthan gum hydrates are prepared at the 1–2% level by weight, with 1.5% being preferred. All the propylene glycol may be used at this stage, or some may be added to the pre-mill vessel if desired.

Stock Solution A, the dispersant, deionized water, and the antifoam were added to a pre-mill vessel. Any propylene glycol not used in the preparation of Solution C can be added here as well. The contents were mixed until homogeneous. The full amount of Solution B can be added at this stage or delayed until recovery of the post-mill material.

Next, the spinosad was added slowly under moderate agitation. After the addition was complete, it was necessary to increase shear to prevent floating and assure wetting. To assure appropriate wetting and reduction of spinosad clumps, the use of a stainless steel rotor/stator homogenizer is recommended, with its effluent recirculated back into the pre-mill vessel.

The contents of the pre-mill vessel were displaced to a wet mill operation (stainless steel bead mill, horizontal preferred) to achieve further particle size reduction. The milled material and the mill rinsate were collected in an agitated, tared, stainless steel vessel (post-mill vessel). The amount of post-mill material recovered was recorded and compared relative to theoretical recovery to determine the percent recovery.

From the percent recovery, the exact amount of Solution C (hydrated xanthan gum) necessary to provide the final product was calculated. If Solution B was not added at the pre-mill stage, use the same calculation performed with Solution C to determine the amount of Solution B to add now. The calculated amount of Solution C (and Solution B if necessary) was added to the post-mill material with mild agitation (propeller blade at roughly 500 rpm), and allowed to stir for 1 hour. A sample of final product was taken to assay for viscosity, particle size and specific gravity.

EXAMPLE 6

Aqueous Suspension Formulation of Spinosad (0.2 g/L)

An aqueous suspension containing 0.2 g of spinosad/L was prepared as follows:

| Component | Quantity % w/w | Batch (g) |
|---|---|---|
| Spinosad, technical, 92.1% | 0.02 | 0.03 |
| Dispersant | 0.1 | 0.15 |
| Propylene Glycol | 10 | 15 |
| Surfactant | 2 | 3 |
| Mineral Thickener | 2 | 3 |
| Antimicrobial Agent | 0.2 | 0.3 |
| Xanthan Gum | 0.2 | 0.3 |
| Water, deionized | 85.38 | 128.07 |
| Antifoam | 0.1 | 0.15 |
| | 100 | 150 |

To prepare the 0.2 g/L aqueous suspension, the following steps are taken: spinosad technical grade (0.03 g) is mixed with surfactant (3.0 g), dispersant (0.15 g), deionized water (7.52 g) and antifoam (0.15 g) and wet-milled in a ball mill to form a grind batch.

Separately, a hydrate suspension batch is prepared as follows: add xanthan gum (0.3 g) to propylene glycol (15 g) and antimicrobial agent (0.3 g) with mixing. Add mineral thickener (3 g) to deionized water (120.55 g) with mixing. Allow the xanthan gum to fully disperse within the propylene glycol; then add the xanthan gum/propylene glycol to the hydrated mineral thickener with mixing.

To form the final aqueous suspension product, add the grind batch to a quantity of the hydrate solution sufficient to form an aqueous suspension with a final spinosad concentration of 0.2 g/L.

EXAMPLE 7

Aqueous Suspension Pour-On Formulation of Spinosad (100 g/L) Containing a Substantive Agent An aqueous suspension formulation containing 100 g/L of spinosad and a polyvinyl acetate is prepared. The polyvinyl acetate acts as a sticker/binder component to increase the formulation's adhesion to hair when used as a pour-on. The suspension components are:

| Component | Quantity % w/w | Batch (g) |
|---|---|---|
| Spinosad, technical | 11.04 | 5.52 |
| Dispersant, 44% solution | 8 | 4 |
| Propylene Glycol | 20 | 10 |
| Surfactant | 1 | 0.5 |
| Mineral Thickener | 2 | 1 |
| Polyvinyl Acetate | 10 | 5 |
| Water, deionized | 47.66 | 23.83 |
| Antimicrobial Agent | 0.2 | 0.1 |
| Antifoam | 0.1 | 0.05 |
| | 100 | 50 |

For this formulation, the grind batch is produced by wet-milling the spinosad in 10 g of deionized water containing the surfactant, the dispersant solution, and 0.05 g of the antifoam. The grind batch is rinsed with an additional 5 g of water. Recovery of the grind batch is 90.46%.

The hydrated suspension is formed by mixing the mineral thickener into 8.83 grams of water containing the antimicrobial agent. The polyvinyl acetate is added to the propylene glycol. The mineral thickener hydrate and the polyvinyl acetate/propylene glycol mixture are mixed to form the hydrate suspension.

The hydrated suspension is added to the grind batch and mixed until uniform.

EXAMPLE 8

Aqueous Suspension Pour-on Formulation of Spinosad (100 g/L)

A pour-on formulation containing 100 g/L of spinosad is prepared as follows:

| Component | Quantity % w/w | Batch (g) |
|---|---|---|
| Spinosad, technical | 11.04 | 5.52 |
| Dispersant, 44% solution | 8 | 4 |
| Propylene Glycol | 10 | 5 |
| Surfactant | 1 | 0.5 |
| Mineral Thickener | 2 | 1 |
| Polyvinyl Alcohol, 10% Solution | 20 | 10 |
| Water, deionized | 47.66 | 23.83 |
| Antimicrobial Agent | 0.2 | 0.1 |
| Antifoam | 0.1 | 0.02 |
| | 100 | 50 |

The grind batch is formed by wet-milling the spinosad in 10 g of deionized water containing the surfactant, the dispersant solution, and the antifoam. The grind batch is rinsed with an additional 5 g of water. Recovery of the grind batch is 88.56%.

The 10% (w/w) solution of polyvinyl alcohol (AIRVOL 125™, Air Products) is formed by mixing it in deionized water heated to 96° C. until it is in solution and allowing the solution to cool to room temperature.

The hydrated suspension batch is formed by mixing the propylene glycol, the mineral thickener, the antimicrobial agent, the polyvinyl alcohol and deionized water (8.83 grams).

The final product is formed by adding 88.56 percent of the hydrated suspension to the grind batch and mixing until uniform.

EXAMPLE 9

Aqueous Suspension Formulation of Spinosad (25 g/L) with Polymeric Thickener and Polymeric Dispersant An aqueous suspension of spinosad was prepared as follows:

| Component | Quantity % w/w | Batch (g) |
|---|---|---|
| Spinosad, technical (92%) | 2.6 | 26 |
| Antimicrobial Agent | 0.25 | 2.5 |
| Antifoam | 0.1 | 1 |
| Surfactant | 2 | 20 |
| Polymeric Dispersant | 3 | 30 |
| Polymeric Thickener | 4 | 40 |

-continued

| Component | % w/w | Batch (g) |
|---|---|---|
| Propylene Glycol | 6 | 60 |
| Water, deionized | 82.05 | 820.5 |
| | 100 | 1000 |

The grind batch was formed by wet-milling the spinosad in 64.9 g of deionized water containing the antimicrobial agent, 0.1 g of the antifoam, 2 g of the surfactant, 2 g of the polymeric dispersant and 2.5 g of the polymeric thickener. Recovery of the grind batch was 91%. A typical polymeric surfactant is ATLOX 4894, and a useful polymeric dispersant is ATLOX 4913 (both manufactured by Uniqema).

A letdown batch was separately formed by siring together 0.9 g of the antifoam, 18 g of the surfactant, 28 g of the polymeric dispersant, 37.5 g of the polymeric thickener, the propylene glycol and 755.6 g of deionized water. The final product was formed by adding 819 g of the letdown batch to the grind batch and mixing until uniform.

EXAMPLE 10

Aqueous Suspension Formulation of Spinosad (480 g/L)

An aqueous suspension containing 480 g/L of spinosad is prepared as follows:

| Component | % w/w | Batch (g) |
|---|---|---|
| Spinosad, technical (91.4%) | 49.14 | 196.56 |
| Propylene Glycol | 3 | 12 |
| Surfactant | 3 | 12 |
| Lignosulfonate Dispersant | 14 | 56 |
| Xanthan Gum | 0.05 | 0.2 |
| Mineral Thickener | 0.35 | 1.4 |
| Water, deionized | 29.76 | 119.04 |
| Antimicrobial Agent | 0.2 | 0.8 |
| Antifoam | 0.5 | 2 |
| | 100 | 400 |

Mix the spinosad with the surfactant, the dispersant, deionized water (90.74 g) and 2 g of antifoam, and wet-mill in a ball mill to form a grind batch. A suitable lignosulfonate dispersant is Reax 88B, Westvaco Corporation, Inc. Recovery of the grind batch was 66.20%.

Separately, prepare the hydrate suspension batch as follows: add the xanthan gum to the propylene glycol with mixing, then add the mineral thickener to 28.3 g of deionized water and the antimicrobial agent with mixing. Allow the xanthan gum to fully disperse within the propylene glycol before adding the xanthan gum/propylene glycol to the hydrated mineral thickener with mixing.

The final product is formed by adding 28.27 grams of the hydrated suspension to the grind batch and mixing until uniform.

EXAMPLE 11

Aqueous Suspension Pour-On Formulation of Spinosad (100 g/L) with Sucrose

The following components are used in this formulation:

| Component | % w/w | Batch (g) |
|---|---|---|
| Spinosad, technical (90%) | 9.55 | 28.65 |
| Propylene Glycol | 5 | 15 |
| Surfactant | 1.5 | 4.5 |
| Dispersant, 44% Solution | 8 | 24 |
| Sucrose Solution, 40% | 75.55 | 226.65 |
| Antimicrobial Agent | 0.2 | 0.6 |
| Antifoam | 0.2 | 0.6 |
| | 100 | 300 |

To form the grind batch, combine the spinosad, the surfactant, the dispersant, the antifoam, and the 40% aqueous sucrose solution and wet mill to desired spinosad median particle size. Recover milled material from mill and determine the percent recovery. To the recovered grind material, add the appropriate amount of propylene glycol and antimicrobial agent to bring the final concentration of spinosad to 100 g/L.

EXAMPLE 12

Aqueous Suspension Pour-On Formulation of Spinosad (200 g/L) with Urea

The following components are used in this formulation:

| Component | % w/w | Batch (g) |
|---|---|---|
| Spinosad, technical (90%) | 19.7 | 59.1 |
| Propylene Glycol | 5 | 15 |
| Surfactant | 2 | 6 |
| Dispersant, 44% Solution | 14 | 42 |
| Urea, aqueous solution, 50% | 58.9 | 176.7 |
| Antimicrobial Agent | 0.2 | 0.6 |
| Antifoam | 0.2 | 0.6 |
| | 100 | 300 |

To form the grind batch, combine the spinosad, the surfactant, the dispersant, the antifoam, and the urea solution and wet mill to desired spinosad median particle size. Recover milled material from mill and determine the percent recovery. To the recovered grind material, add the appropriate amount of propylene glycol and antimicrobial agent to bring the final concentration of spinosad to 200 g/L.

What is claimed is:

1. A stable ectoparasiticidal aqueous suspension formulation suitable for administration to animals comprising:
    a) an ectoparasiticidal amount of spinosad, milled to an average particle size of from 1 to 15 microns;
    b) a condensed formaldehyde/naphthalene sulfonic acid or salt thereof dispersant, wherein the spinosad:dispersant weight ratio is 3:1 to 1:5;
    c) 0.3 to 5 weight percent of a mineral thickener;
    d) an antimicrobial agent acceptable for topical veterinary applications in an amount effective to prevent microbial growth in the suspension;

e) propylene glycol;
f) 0.05 to 3 weight percent of xanthan gum;
g) 0.1 to 10 weight percent of at least one surfactant;
h) an antifoam agent; and
i) water; wherein
said formulation is chemically and physically stable.

2. A formulation of claim 1 wherein the average particle size of spinosad is about 2 to about 7 microns.

3. A formulation of claim 2 wherein the amount of spinosad is from about 0.02 to about 50 weight percent of the formulation.

4. A formulation of claim 3 wherein the amount of spinosad is from about 2 to about 5 weight percent of the formulation.

5. A formulation of claim 4 wherein the surfactant is present in an amount of from about 0.1 to about 5 weight percent of the formulation.

6. A formulation of claim 5 wherein the spinosad is present in an amount of about 25 grams per liter of the formulation.

7. An article of manufacture, comprising packaging material and a formulation for controlling an ectoparasite infestation on a small ruminant or companion animal contained within said packaging material, wherein said formulation comprises:

a unit dose of a formulation of claim 1; and wherein said packaging material comprises a label or package insert with instructions for administering the dose to the animal.

8. A method of controlling an ectoparasite infestation on a small ruminant or companion animal, comprising administering to the animal an effective amount of formulation of claim 1.

9. The method of claim 8 wherein the formulation is applied to the head, neck, shoulders or back of the animal by a spot-on or pour-on protocol.

* * * * *